United States Patent
Takahashi

[11] Patent Number: 6,154,517
[45] Date of Patent: Nov. 28, 2000

[54] FLUORESCENT X-RAY SPECTROSCOPE

[75] Inventor: Haruo Takahashi, Chiba, Japan

[73] Assignee: Seiko Instruments, Inc., Chiba, Japan

[21] Appl. No.: 09/064,332

[22] Filed: Apr. 22, 1998

[30] Foreign Application Priority Data

Apr. 25, 1997 [JP] Japan .................................... 09-109705
Jan. 23, 1998 [JP] Japan .................................... 10-011536

[51] Int. Cl.[7] .............................................. G01N 22/223
[52] U.S. Cl. .................................. 378/46; 378/42; 378/44
[58] Field of Search ................................. 378/42, 46, 44

[56] References Cited

U.S. PATENT DOCUMENTS 5,289,386  2/1994  Anderson ................................ 364/498
5,754,620  5/1998  Hossain et al. ............................ 378/45

*Primary Examiner*—David V. Bruce
*Assistant Examiner*—Michael J. Schwartz
*Attorney, Agent, or Firm*—Loeb & Loeb, LLP

[57] ABSTRACT

Display is made of the spectrums of the fluorescent X-rays by using the ordinate axis as representing the square root of a fluorescent X-ray intensity and using the abscissa axis as representing the energy of the fluorescent X-rays.

7 Claims, 4 Drawing Sheets

FLUORESCENT X-RAY SPECTROSCOPE

BACKGROUND OF THE INVENTION

The present invention relates to a fluorescent X-ray spectroscope.

In a fluorescent X-ray spectroscopy, although the automation of the spectrum analysis has been proceeding, there is still a case where it is needed to confirm with the naked eyes the position and shape of a peak on spectrums of fluorescent X-rays obtained as a result of measurement thereof. Therefore, a method for displaying spectrums of fluorescent X-rays is a very important factor for a fluorescent X-ray spectroscope.

The most typical display method of a conventional fluorescent X-ray spectroscope is a method of display made with the energy of fluorescent X-rays being plotted along the abscissa axis and the intensity of fluorescent X-rays being plotted along the ordinate axis. Further, it was arranged that fine portions could also be seen by changing the magnifications of the ordinate and abscissa axes.

In the case of using this method, when trying to see a very small peak, in many cases a large peak does not completely fall within a display range and so it is difficult to read the positional relationship thereof with a very small peak. In such a case, there has hitherto been adopted a method of display made with the ordinate axis being used as representing the logarithm of the intensity.

In the present invention, there is provided a method for solving the following two problems in view of the conventional technique described under the preceding item.

The first problem is explained. Although it is possible to visually simultaneously compare with each other the peaks whose intensity levels are greatly different from each other by using the ordinate axis as representing the logarithm of the fluorescent X-ray intensity, the shape of each peak greatly differs from that in the case where the ordinate axis is used as representing the fluorescent X-ray intensity itself. Therefore, there was the drawback that difficulties arose in intuitionally grasping the shapes of the peaks and the intensity levels. According to the present invention, there is provided a fluorescent X-ray spectroscope having the function of enabling the visual and simultaneous comparison between the peaks greatly differrring from each other in terms of the intensity level to be made while suppressing the changes in shape of the peaks.

The second problem is explained. This concerns the problem that arises where spectrums having therein a positive intensity and a negative intensity therein in a form of co-existence must be displayed as in the case of expressing the difference between two spectrums. In such a case, when it is wanted to simultaneously display peaks whose intensity levels greatly differ from each other, the attempt to use a method wherein the logarithm of the fluorescent X-ray intensity is plotted along the ordinate axis results in a failure to display excellently due to the fact that since the logarithm is discontinuous at the value of 0, the ordinate axis becomes discontinuous with the value of 0 as a border. According to the present invention, there is provided a fluorescent X-ray spectroscope having the function of simultaneously displaying peaks of different intensity levels in a form wherein these peaks can be easily discriminated even where the spectrums are ones wherein a positive intensity and a negative intensity co-exit.

SUMMARY OF THE INVENTION

The above-described problems have been solved by causing a spectrum display portion of the fluorescent X-ray spectroscope to have the following function.

Display is made by using the ordinate axis as representing the square root of a fluorescent X-ray intensity and using the abscissa axis as representing the energy of the fluorescent X-rays, provided, however, that when displaying a negative value, the square root of the absolute value of the fluorescent X-ray intensity is multiplied by (−1).

DETAILED DESCRIPTION OF THE INVENTION

Figure 1:
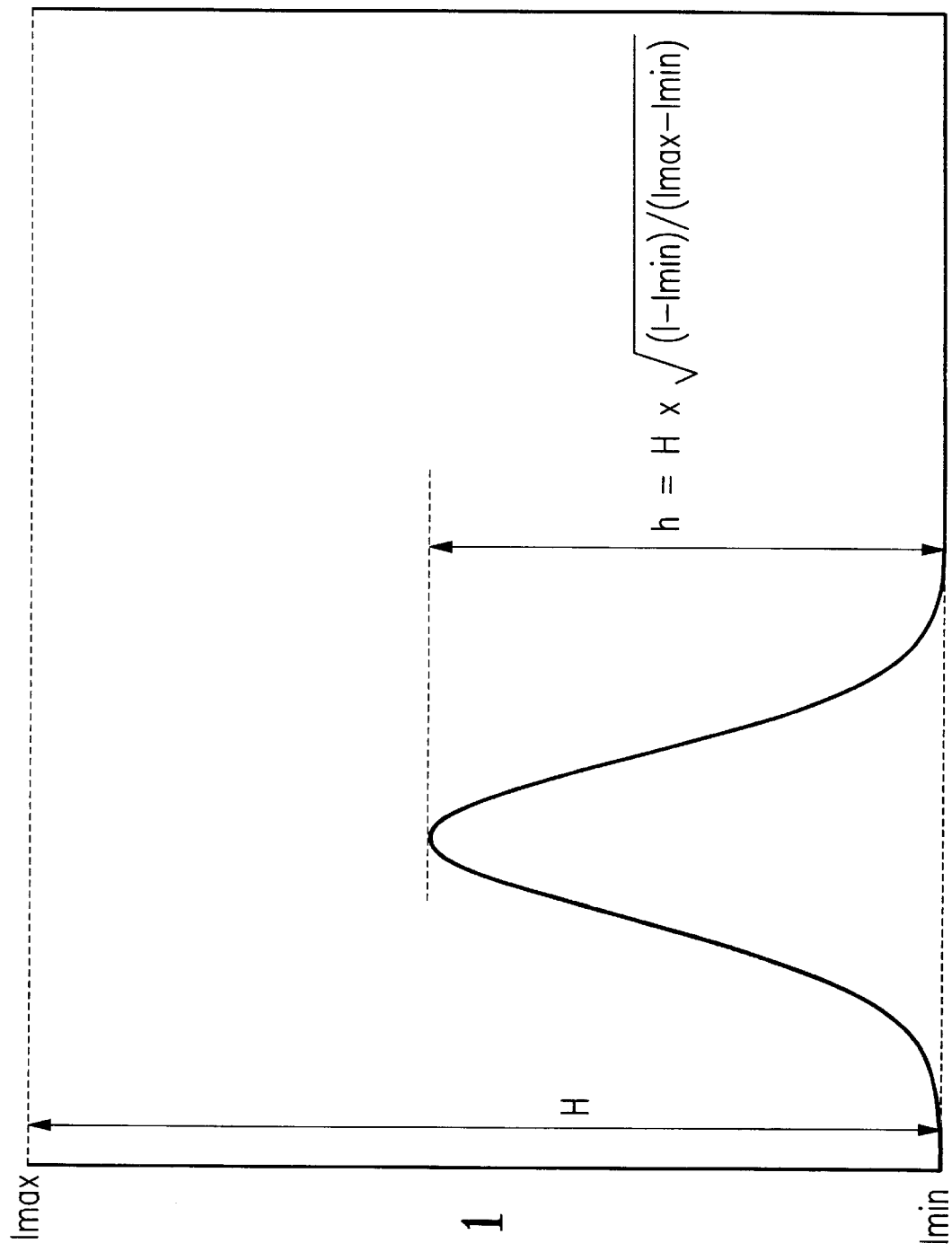
FIG. 1 is a diagram illustrating a display method that is used in the present invention (a first one).

In a fluorescent X-ray spectroscope comprising an X-ray generator for generating X-rays radiated onto a sample, detector means for detecting fluorescent X-rays coming out from the sample by radiating of X-rays with respect thereto, and display means for displaying spectrums of the detected X-rays, the spectrums are displayed by the following method. FIG. 1 is an illustration thereof. In FIG. 1, in a case where depicting a range from the intensity Imax to the intensity Imin in a spectrum depiction region having a height of H, when it is assumed that a fluorescent X ray that corresponds to a certain energy has an intensity of I, the height h corresponding to the intensity I in the graphic diagram is determined according to the equation [1].

$$h = H \times \sqrt{\{(I-Imin)/(Imax-Imin)\}} \qquad [1]$$

provided, however, that 0 ≦ Imin < Imax

This operation is performed with respect to all energies to be displayed to thereby depict spectrums.

Figure 4:
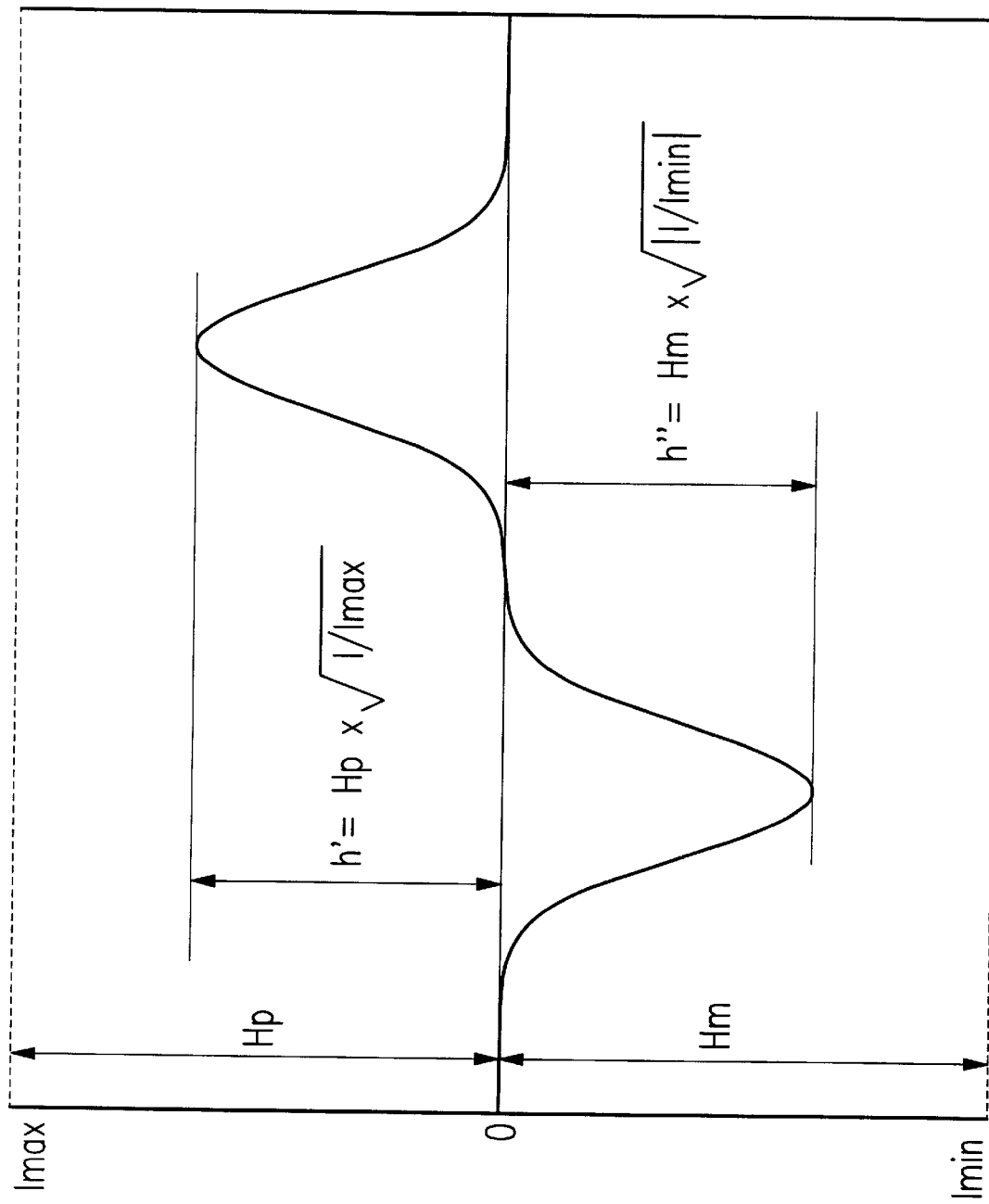

Next, an example of a case where display is made of spectrums wherein positive values and negative values co-exist will be explained with reference to FIG. 4. In a case where displaying the difference between the two spectrums obtained as a result of measurement in the above-described fluorescent X-ray spectroscope, spectrums wherein positive values and negative values co-exist must be displayed. When using the equation [1] as is in such a case, there is a case where the height h becomes an imaginary number. On this account, under the assumption that h' represents the height in the graphic diagram in the case where the intensity I is positive and h" represents the height in the graphic diagram in the case where the intensity I is negative, the h' and h" are given by the equation [2].

$$h' = Hp \times \sqrt{(I/Imax)} \quad (I \geq 0)$$
$$h'' = -Hm \times \sqrt{(|I/Imin|)} \quad (I < 0)$$
[2]

provided, however, that Imin<0<Imax
Here, Hp represents the height of the spectrum depiction region in a range of from the intensity 0 to the intensity Imax. Also, Hm represents the height of the spectrum depiction region in a range of from the intensity 0 to the intensity Imin. Here, assuming that H represents the spectrum depiction region of the display means, $$Hp = H \times Imax / (Imax + |Imin|),$$
$$Hm = H \times |Imin| / (Imax + |Imin|).$$

The effect of the present invention will now be explained with reference to FIGS. 2 and 3 in which comparison is made between the present invention and the conventional technique.

Figure 2:
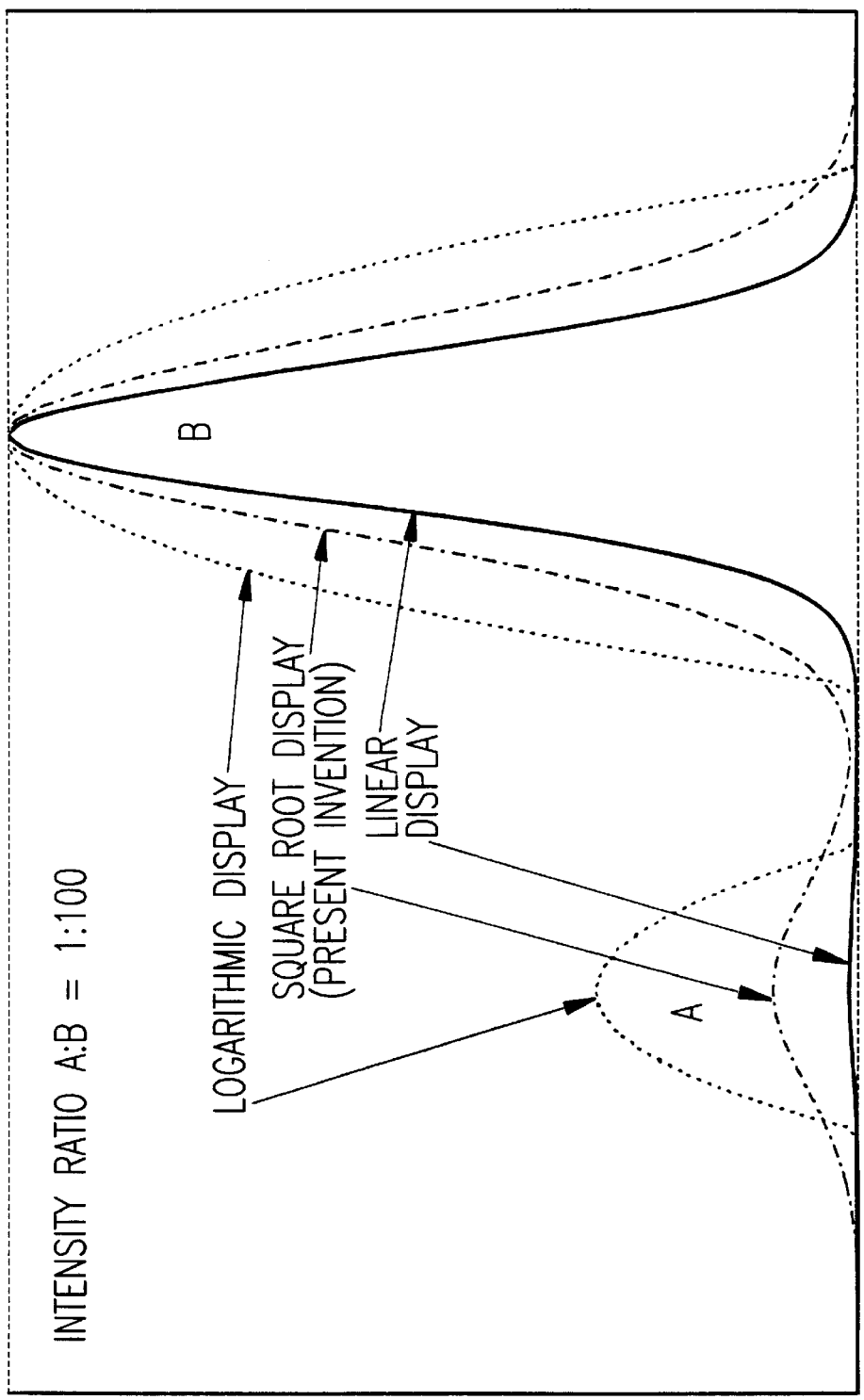
FIG. 2 is a diagram illustrating a comparison with a conventional technique.

FIG. 2 is a graphic diagram wherein the display method provided by the fluorescent X-ray spectroscope of the first embodiment and the method provided by the conventional fluorescent X-ray spectroscope are superimposed one over the other for comparison. While in FIG. 2 two peaks having an intensity ratio of 1:100 are displayed, in the method indicated as "Linear Display" wherein the intensity itself is used along the ordinate axis, when setting the display scale so that a peak B may fall within the range of the graphic diagram, it is difficult to confirm a peak A. Also, in the method indicated as "Logarithmic Display" wherein the logarithm of the fluorescent X-ray intensity is used along the ordinate axis, although the existence of the peak A becomes prominent, it is seen that the shapes of the peaks are greatly different. In contrast to these conventional techniques, in the fluorescent X-ray spectroscope according to the present invention, it is possible to make the display indicated in FIG. 2 as "Square Root Display". It is seen that in the display made according to the present invention the existence of the peak A can be confirmed without difficulty and the changes in shape of the peaks are suppressed to a degree that is much lower than that in the case of the "Logarithmic Display".

Figure 3:
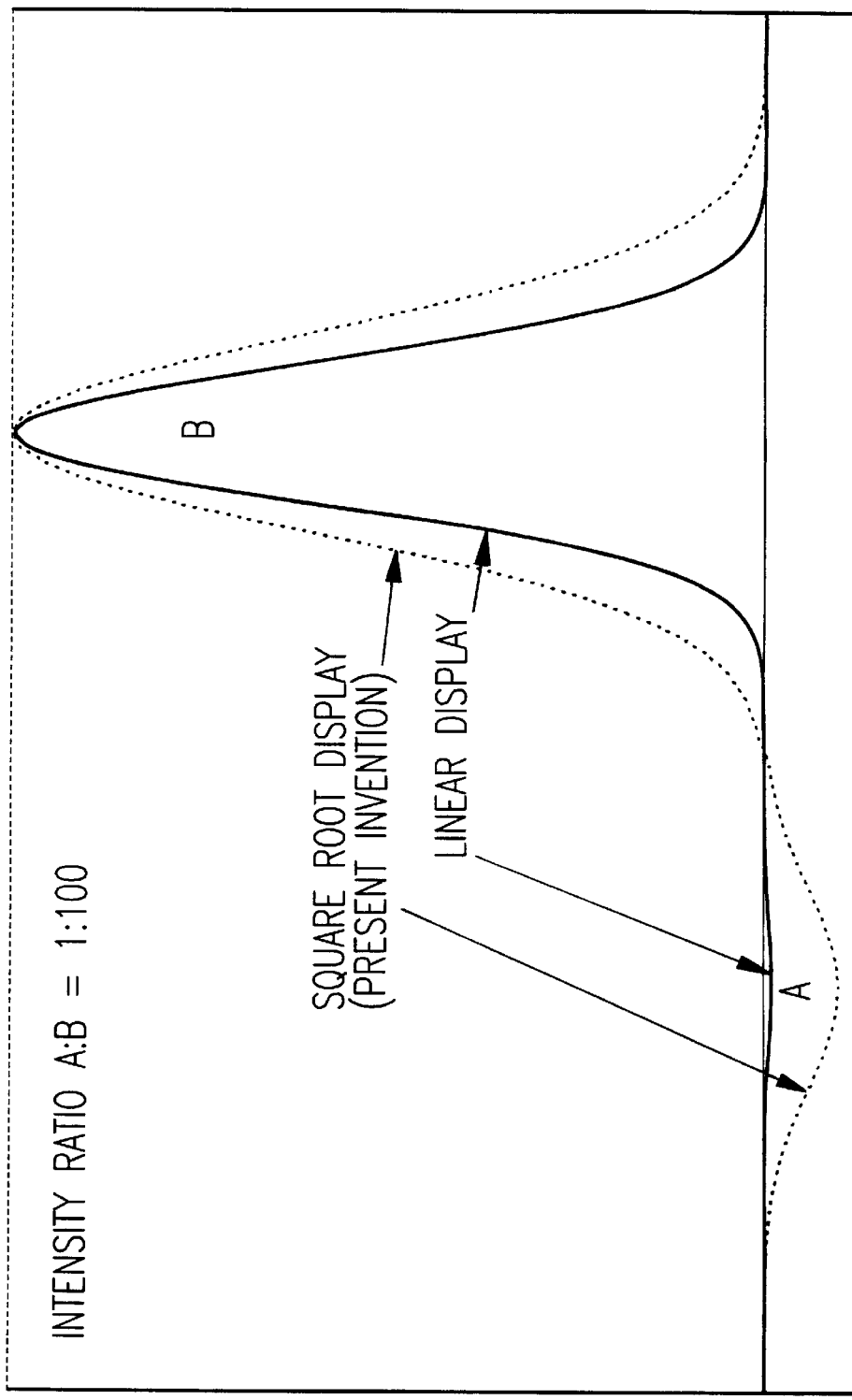
FIG. 3 is a diagram illustrating a comparison with the conventional technique, wherein positive values and negative values co-exist. And, FIG. 4 is a diagram illustrating a display method that is used in the present invention (a second one).

FIG. 3 is a graphic diagram wherein the display method provided by the fluorescent X-ray spectroscope of the second embodiment and the method provided by the conventional fluorescent X-ray spectroscope are superimposed one over the other for comparison. In a case where positive values and negative values co-exist as in this case, since there could not be used the method wherein the logarithm of the fluorescent X-ray intensity was plotted along the ordinate axis, there was no way but to use the intensity itself of the fluorescent X-rays as far as concerning the ordinate axis. However, it is seen from FIG. 3 that the peaks whose intensity levels greatly differ from each other and which could not be simultaneously easily discriminatingly displayed in the prior art can be displayed as enabling easy discrimination by the fluorescent X-ray spectroscope of the invention.

For the above-described reasons, in the fluorescent X-ray spectroscope of the present invention, the visual confirmation of the position and shape of a peak which is a very important step when analyzing the spectrums of the measured fluorescent X-rays being arranged to be very easily made, the present invention can greatly contribute to performing an efficient analysis.

What is claimed is:

1. A fluorescent X-ray spectroscope comprising an X-ray generator for generating X-rays radiated onto a sample, detector means for detecting fluorescent X-rays coming out from the sample by radiating of X-rays with respect thereto, and display means for displaying spectrums of the detected X-rays, characterized in that the spectrums obtained as a result of measurement are displayed with the square root of a fluorescent X-ray intensity being plotted along the ordinate axis and the energy of the fluorescent X-rays being plotted along the abscissa axis.

2. A fluorescent X-ray spectroscope comprising an X-ray generating means for generating X-rays radiated onto a sample, detector means for detecting fluorescent X-rays coming out from the sample by radiating of X-rays with respect thereto, and display means for displaying spectrums of the detected X-rays, characterized in that the difference between two spectrums obtained as a result of measurement is displayed with the square root of a fluorescent X-ray intensity being plotted along a positive direction of the ordinate axis, a value obtained by multiplying the square root of the absolute value of the fluorescent X-ray intensity by (−1) being plotted along a negative direction of the ordinate axis, and the energy of the fluorescent X-rays being plotted along the abscissa axis.

3. In a fluorescent x-ray spectroscope comprising a detector for measuring intensities of fluorescent x-rays from a sample and a display for displaying spectra of the fluorescent x-rays, a method of displaying a fluorescent x-ray spectrum comprising:

plotting the square root of the fluorescent x-ray intensity against fluorescent x-ray energy.

4. The method of claim 3, further comprising subtracting an offset from measured fluorescent x-ray intensities before plotting the square root of the intensity.

5. In a fluorescent x-ray spectroscope comprising a detector for measuring intensities of fluorescent x-rays from a sample and a display for displaying spectra of the fluorescent x-rays, a method of displaying a difference spectrum between two spectra comprising: plotting a product of the sign of a difference of the two fluorescent intensities and the square root of the absolute value of the difference of the two fluorescent x-ray intensities against fluorescent x-ray energy.

6. A method of visually displaying data represented by first and second parameters, the data having a plurality of positive and/or negative peaks if the second parameter is plotted against the first parameter on a linear scale, the ratio of the heights of at least some of the peaks being greater than about 100, the method comprising:

plotting a product of the sign of the second parameter and the square root of the absolute value of the second parameter against the first parameter.

7. A method of visually displaying data, comprising:

obtaining data represented by first and second parameters, the data having a plurality of positive and/or negative peaks if the second parameter is plotted against the first parameter on a linear scale, the ratio of the heights of at least some of the peaks being greater than about 100; and plotting a product of the sign of the second parameter and the square root of the absolute value of the second parameter against the first parameter.

* * * * *